(12) United States Patent
Calhoun et al.

(10) Patent No.: US 11,278,389 B2
(45) Date of Patent: Mar. 22, 2022

(54) METHODS AND DEVICES FOR TREATING AN EYE USING A FILTER

(71) Applicant: J.D. Franco & Company, Plano, TX (US)

(72) Inventors: Michael Calhoun, Lighthouse Point, FL (US); Jeff Franco, Plano, TX (US); Kemal Schankereli, Stillwater, MN (US)

(73) Assignee: J.D. Franco & Co., LLC, Plano, TX (US)

( * ) Notice: Subject to any disclaimer, the term of this patent is extended or adjusted under 35 U.S.C. 154(b) by 335 days.

(21) Appl. No.: 16/467,318

(22) PCT Filed: Dec. 7, 2017

(86) PCT No.: PCT/US2017/065004
§ 371 (c)(1),
(2) Date: Jun. 6, 2019

(87) PCT Pub. No.: WO2018/106858
PCT Pub. Date: Jun. 14, 2018

(65) Prior Publication Data
US 2019/0307547 A1    Oct. 10, 2019

Related U.S. Application Data

(60) Provisional application No. 62/431,807, filed on Dec. 8, 2016.

(51) Int. Cl.
*A61F 2/01* (2006.01)
*A61B 17/22* (2006.01)
(Continued)

(52) U.S. Cl.
CPC ........ *A61F 2/013* (2013.01); *A61B 17/22031* (2013.01); *A61F 2/06* (2013.01);
(Continued)

(58) Field of Classification Search
CPC ........ A61F 2/01; A61F 2/0103; A61F 2/0105; A61F 2/0108; A61F 2/011; A61F 2/012;
(Continued)

(56) References Cited

U.S. PATENT DOCUMENTS 2,690,595 A    10/1954    Raiche
3,367,101 A    2/1968    Garnet et al.
(Continued)

FOREIGN PATENT DOCUMENTS

WO    WO 98/52639 A1    11/1998
WO    WO 98/53761 A1    12/1998
(Continued)

OTHER PUBLICATIONS

Altinbas, N.K. et al, "Effect of Carotid Artery Stenting on Ophthalmic Artery Flow Patterns," Journal of Ultrasound Medicine, 2014; 33: pp. 629-638.
(Continued)

*Primary Examiner* — Wade Miles
*Assistant Examiner* — Kankindi Rwego
(74) *Attorney, Agent, or Firm* — Bookoff McAndrews, PLLC (57) ABSTRACT

A method for treating at least one of an ophthalmic artery or an ostium between the ophthalmic artery and an internal carotid artery of a subject may include delivering a microcatheter to a location within vasculature of the subject. The method may further include delivering a filter to a location within at least one of the ophthalmic artery or the ostium and transitioning the filter between a first delivery configuration and a second deployed configuration. Further, the method may include deploying a stent to a location within the internal carotid artery.

17 Claims, 3 Drawing Sheets

(51) Int. Cl.
  *A61F 2/966* (2013.01)
  *A61F 2/82* (2013.01)
  *A61F 2/90* (2013.01)
  *A61F 2/06* (2013.01)
  *A61F 2/00* (2006.01)
  *A61M 25/00* (2006.01)

(52) U.S. Cl.
  CPC ............ *A61F 2/82* (2013.01); *A61F 2/90* (2013.01); *A61F 2/966* (2013.01); *A61F 2/011* (2020.05); *A61F 2002/0081* (2013.01); *A61F 2002/016* (2013.01); *A61F 2002/018* (2013.01); *A61F 2250/0098* (2013.01); *A61M 2025/0042* (2013.01)

(58) Field of Classification Search
  CPC .. A61F 2/013; A61F 2/014; A61F 2/02; A61F 2/06; A61F 2/82; A61F 2/844; A61F 2/848; A61F 2/852; A61F 2/856; A61F 2/86; A61F 2/885; A61F 2/89; A61F 2/90; A61F 2/966; A61F 2002/0081; A61F 2002/015; A61F 2002/016; A61F 2002/018; A61F 2002/9665; A61F 9/0017; A61F 9/007; A61F 9/00709; A61F 9/00781; A61F 2250/0098; A61M 2025/0042; A61B 17/22031; A61B 17/221; A61B 2017/22034; A61B 2017/22035; A61B 2017/22038; A61B 2017/2212; A61B 2017/2215; A61B 2017/2217
  USPC ....................................................... 623/1.11
  See application file for complete search history.

(56) References Cited

U.S. PATENT DOCUMENTS

| | | | |
|---|---|---|---|
| 3,435,826 A | 4/1969 | Fogarty | |
| 4,403,612 A | 9/1983 | Fogarty | |
| 4,445,897 A | 5/1984 | Ekbladh et al. | |
| 4,926,858 A | 5/1990 | Gifford, III et al. | |
| 5,026,384 A | 6/1991 | Farr et al. | |
| 5,176,693 A | 1/1993 | Pannek, Jr. | |
| 5,336,234 A | 8/1994 | Vigil et al. | |
| 5,395,311 A | 3/1995 | Andrews | |
| 5,419,761 A | 5/1995 | Narayanan et al. | |
| 5,709,701 A | 1/1998 | Parodi | |
| 5,820,595 A | 10/1998 | Parodi | |
| 5,897,567 A | 4/1999 | Ressemann et al. | |
| 5,972,019 A * | 10/1999 | Engelson ............ A61B 17/221 606/200 | |
| 6,146,370 A | 11/2000 | Barbut | |
| 6,168,579 B1 * | 1/2001 | Tsugita ............ A61B 17/12109 604/96.01 | |
| 6,206,868 B1 | 3/2001 | Parodi | |
| 6,258,115 B1 * | 7/2001 | Dubrul ............ A61F 2/88 606/200 | |
| 6,302,908 B1 | 10/2001 | Parodi | |
| 6,336,933 B1 | 1/2002 | Parodi | |
| 6,344,054 B1 | 2/2002 | Parodi | |
| 6,413,235 B1 | 7/2002 | Parodi | |
| 6,423,032 B2 | 7/2002 | Parodi | |
| 6,540,712 B1 | 4/2003 | Parodi et al. | |
| 6,595,980 B1 | 7/2003 | Barbut | |
| 6,623,471 B1 | 9/2003 | Barbut | |
| 6,626,861 B1 | 9/2003 | Hart et al. | |
| 6,641,573 B1 | 11/2003 | Parodi | |
| 6,645,222 B1 | 11/2003 | Parodi et al. | |
| 6,824,558 B2 | 11/2004 | Parodi | |
| 6,827,726 B2 | 12/2004 | Parodi | |
| 6,837,881 B1 | 1/2005 | Barbut | |
| 6,855,162 B2 | 2/2005 | Parodi | |
| 6,902,540 B2 | 6/2005 | Dorros et al. | |
| 6,905,490 B2 | 6/2005 | Parodi | |
| 6,908,474 B2 | 6/2005 | Hogendijk et al. | |
| 6,929,634 B2 | 8/2005 | Dorros et al. | |
| 6,936,053 B1 | 8/2005 | Weiss | |
| 6,936,060 B2 | 8/2005 | Hogendijk et al. | |
| 7,214,201 B2 | 5/2007 | Burmeister et al. | |
| 7,235,095 B2 | 6/2007 | Haverkost et al. | |
| 7,309,334 B2 | 12/2007 | Von Hoffmann | |
| 7,604,612 B2 | 10/2009 | Ressemann et al. | |
| 7,806,906 B2 | 10/2010 | Don Michael | |
| 7,867,273 B2 | 1/2011 | Pappas et al. | |
| 7,901,445 B2 | 3/2011 | Walker et al. | |
| 7,927,347 B2 | 4/2011 | Hogendijk et al. | |
| 8,157,760 B2 | 4/2012 | Carido et al. | |
| 8,353,850 B2 | 1/2013 | Ressemann et al. | |
| 8,414,516 B2 | 4/2013 | Chang | |
| 8,545,432 B2 | 10/2013 | Renati et al. | |
| 8,834,404 B2 | 9/2014 | Beaudin | |
| 8,852,226 B2 | 10/2014 | Gilson et al. | |
| 8,863,631 B1 | 10/2014 | Janardhan et al. | |
| 9,078,682 B2 | 7/2015 | Lenker et al. | |
| 9,241,699 B1 | 1/2016 | Kume et al. | |
| 9,259,215 B2 | 2/2016 | Chou et al. | |
| 9,265,512 B2 | 2/2016 | Garrison et al. | |
| 9,987,164 B2 | 6/2018 | Calhoun | |
| 2001/0001114 A1 | 5/2001 | Tsugita et al. | |
| 2002/0087128 A1 | 7/2002 | Paques et al. | |
| 2002/0143291 A1 | 10/2002 | Slater | |
| 2002/0151922 A1 | 10/2002 | Hogendijk et al. | |
| 2003/0023200 A1 | 1/2003 | Barbut et al. | |
| 2003/0023227 A1 | 1/2003 | Zadno-Azizi et al. | |
| 2003/0199802 A1 | 10/2003 | Barbut | |
| 2003/0199819 A1 | 10/2003 | Beck | |
| 2003/0203958 A1 | 10/2003 | Kunz et al. | |
| 2005/0149117 A1 | 7/2005 | Khosravi et al. | |
| 2006/0136022 A1 | 6/2006 | Wong, Jr. et al. | |
| 2006/0259132 A1 | 11/2006 | Schaffer et al. | |
| 2007/0026035 A1 | 2/2007 | Burke et al. | |
| 2008/0027519 A1 | 1/2008 | Guerrero | |
| 2008/0243229 A1 | 10/2008 | Wallace et al. | |
| 2009/0018455 A1 | 1/2009 | Chang | |
| 2009/0024072 A1 | 1/2009 | Criado et al. | |
| 2009/0030323 A1 | 1/2009 | Fawzi et al. | |
| 2010/0125244 A1 | 5/2010 | McAndrew | |
| 2011/0143993 A1 | 6/2011 | Langer et al. | |
| 2011/0152683 A1 | 6/2011 | Gerrans et al. | |
| 2011/0152998 A1 | 6/2011 | Berez et al. | |
| 2011/0160762 A1 | 6/2011 | Hogendijk et al. | |
| 2012/0046679 A1 | 2/2012 | Patel et al. | |
| 2012/0078287 A1 | 3/2012 | Barbut | |
| 2012/0101510 A1 | 4/2012 | Lenker et al. | |
| 2013/0035628 A1 | 2/2013 | Garrison et al. | |
| 2013/0197621 A1 | 8/2013 | Ryan et al. | |
| 2013/0281788 A1 | 10/2013 | Garrison | |
| 2013/0282099 A1 * | 10/2013 | Huynh ............ A61F 2/91 623/1.12 | |
| 2014/0154246 A1 | 6/2014 | Robinson et al. | |
| 2015/0032147 A1 * | 1/2015 | Janardhan ........ A61B 17/12109 606/200 | |
| 2015/0313607 A1 | 11/2015 | Zhadkevich | |
| 2015/0359549 A1 * | 12/2015 | Lenker ............ A61B 17/12118 600/585 | |
| 2015/0366580 A1 | 12/2015 | Lenihan et al. | |
| 2016/0166754 A1 | 6/2016 | Kassab et al. | |

FOREIGN PATENT DOCUMENTS

| | | |
|---|---|---|
| WO | WO 00/54673 A1 | 9/2000 |
| WO | WO 03/018085 A2 | 3/2003 |
| WO | WO 2007/103464 A2 | 9/2007 |
| WO | WO 2014/022866 A1 | 2/2014 |
| WO | WO 2016/109586 A1 | 7/2016 |

OTHER PUBLICATIONS

Ambarki, K. et al., "Blood Flow of Ophthalmic Artery in Healthy Individuals Determined by Phase-Contrast Magnetic Resonance (56) References Cited

OTHER PUBLICATIONS

Imaging," Investigative Ophthalmology & Visual Science, 2013; 54: pp. 2738-2745.
Hwang, G. et al., "Reversal of Ischemic Retinopathy Following Balloon Angioplasty of a Stenotic Ophthalmic Artery." Journal of Neuro-Ophthalmology 30.3, 2010, pp. 228-230.
Kane, A.G. et al., "Reduced Caliber of the Internal Carotid Artery: A Normal Finding with Ipsilateral Absence or Hypoplasia of the A1 Segment," American Journal of Neuroradiology, 1996; 17: pp. 1295-1301.
Kawa, M.P. et al., "Complement System in Pathogenesis of AMD: Dual Player in Degeneration and Protection of Retinal Tissue," Hindawi Publishing Corporation, Journal of Immunology Research, vol. 2014, Article ID 483960, 12 pages.
Klein, R. et al., "Vasodilators, Blood Pressure-Lowering Medications, and Age-Related Macular Degeneration," American Academy of Ophthalmology, 2014, vol. 121, Issue 8, pp. 1604-1611.
Kooragayala, K. et al., "Quanitification of Oxygen Consumption in Retina Ex Vivo Demonstrates Limited Reserve Capacity of Photoreceptor Mitochondria," Investigative Ophthalmology & Visual Science, 2015; 56: pp. 8428-8436.
Krejza, J. et al., "Carotid Artery Diameter in Men and Women and the Relation to Body and Neck Size," Stroke, 2006; 3 pages.
Lanzino, G. et al., "Treatment of Carotid Artery Stenosis: Medical Therapy, Surgery, or Stenting?," Mayo Clinic Proceedings, Apr. 2009; 84(4), pp. 362-368.
Michalinos, A. et al., "Anatomy of the Ophthalmic Artery: A Review concerning Its Modern Surgical and Clinical Applications," Hindawi Publishing Corporation, Anatomy Research International, vol. 2015, Article ID 591961, 8 pages.
Paques, M. et al., "Superselective ophthalmic artery fibrinolytic therapy for the treatment of central retinal vein occlusion." British Journal of Ophthalmology, 2000, 84: 1387-1391.
Tan, P.L. et al., "AMD and the alternative complement pathway: genetics and functional implications," Human Genomics, 2016, 10:23, 13 pages.
Xu, H. et al., "Targeting the complement system for the management of retinal inflammatory and degenerative diseases," European Journal of Pharmacology, 2016, 787, pp. 94-104.
Yamane, T. et al., "The technique of ophthalmic arterial infusion therapy for patients with intraocular retinoblastoma," International Journal of Clinical Oncology, Apr. 2004; vol. 9, Issue 2, pp. 69-73.
Zeumer, H. et al., "Local intra-arterial fibrinolytic therapy in patients with stroke: urokinase versus recombinant tissue plagminogen activator (r-TPA)," Neuroradiology, 1993; 35: pp. 159-162.
Zipfel, P.F., et al., "The Role of Complement in AMD," Inflammation and Retinal Disease: Complement Biology and Pathology, Advances in Experimental Medicine and Biology, 2010, 703, pp. 9-24.
Examination Report No. 2 for AU Application No. 2013296195, dated Jun. 27, 2017 (6 pages).
Notice of Allowance for KR 20157005602, dated Sep. 25, 2017 (3 pages).
Loh, K. et al., "Prevention and management of vision loss relating to facial filler injections." Singapore Medical Journal, 2016; 57(8): 438-443.
International Search Report and Written Opinion for International Application No. PCT/US2017/0051551, dated Dec. 15, 2017 (14 pages).
International Search Report and Written Opinion for International Application No. PCT/US2017/0052901, dated Dec. 8, 2017 (9 pages).
Bird, B. et al., "Anatomy, Head and Neck, Ophthalmic Arteries," NCBI Bookshelf, a service of the National Library of Medicine, National Institutes of Health, Oct. 27, 2018, 5 pages. www.ncbi.nlm.nih.gov/books/NBK482317/.
Hattenbach, L. et al., "Experimental Endoscopic Endovascular Cannulation: A Novel Approach to Thrombolysis in Retinal Vessel Occlusion," Investigative Ophthalmology & Visual Science, Jan. 2012, vol. 53, No. 1, pp. 42-46.
Khan, T.T. et al., "An Anatomical Analysis of the Supratrochlear Artery: Considerations in Facial Filler Injections and Preventing Vision Loss," Aesthetic Surgery Journal, 2017, vol. 37(2), pp. 203-208.
Schumacher, M. et al., "Intra-arterial fibrinolytic therapy in central retinal artery occlusion," Neuroradiology (1993) 35: pp. 600-605.
Schwenn, O.K. et al., "Experimental Percutaneous Cannulation of the Supraorbital Arteries: Implication for Future Therapy," Investigative Ophthalmology & Visual Science, May 2005, vol. 46, No. 5, pp. 1557-1560.
Wang, R. et al., "Evaluation of Ophthalmic Artery Branch Retrograde Intervention in the Treatment of Central Retinal Artery Occlusion (CRAO)," Medical Science Monitor, 2017, 23: pp. 114-120.
Zhao, W. et al. "Three-Dimensional Computed Tomographic Study on the Periorbital Branches of the Ophthalmic Artery: Arterial Variations and Clinical Relevance," Aesthetic Surgery Journal, 2018, pp. 1-9.
International Search Report and Written Opinion for corresponding PCT/US2013/053670, dated Dec. 26, 2013 (16 pp.).
Hayreh et al., "Ocular Arterial Occlusive Disorders and Carotid Artery Disease," American Academy of Ophthalmology, 2017; vol. 1, No. 1: pp. 12-18.
Hayreh et al., "The Ophthalmic Artery," Brit. J. Ophthal., 1962; 46, 65: pp. 65-98.

\* cited by examiner

METHODS AND DEVICES FOR TREATING AN EYE USING A FILTER

CROSS-REFERENCE TO RELATED APPLICATIONS

This application is the U.S. national phase entry under 35 U.S.C. § 371 of International Application No. PCT/US2017/065004, filed Dec. 7, 2017. Additionally, this application claims the benefit under 35 U.S.C § 119(e) of U.S. Provisional Application No. 62/431,807, filed Dec. 8, 2016, the entirety of which is incorporated by reference herein.

FIELD

Disclosed herein is one or more filter apparatuses configured for deployment in one or more vascular structures providing blood flow to or around the eye, e.g., the internal carotid artery (ICA) and the ophthalmic artery (OA). The present disclosure relates to treating eye diseases and conditions.

BACKGROUND

Diseases of the eye, specifically age-related macular degeneration (AMD), glaucoma and diabetic retinopathy affect a large percentage of the population. In the example of AMD, currently approved treatments include surgically implanting a miniature lens (e.g., a VisionCare lens), monthly injections of the anti-cancer drug Avastin into the eye, injecting a therapeutic antibody into the eye (e.g., Macugen, pegaptanib), and/or photo or laser treatment to destroy or treat "abnormal" blood vessels. However, these therapies are deficient in one or more aspects, necessitating improved approaches. In part, most of the diseases of the eye are treated by treating one or more symptoms, but failing to address the underlying cause(s) of the disease or condition.

In a general sense, the pathogenesis of some of these eye diseases and conditions is similar if not the same as those seen for cardiac diseases and for abdominal aorta conditions. However, the anatomy of the vasculature behind the eye is smaller, includes more branches, and includes more odd angles in the blood flow pathway, e.g., the angle where one artery meets or joins another is sometimes quite severe, sharp, etc. That is, the anatomy of the vasculature behind the eye includes a more tortuous blood flow pathway than the anatomy of the vasculature of other portions of the cardiac system, including around the abdominal aorta.

While not intending to be restricted to any particular theory of operation, function, or causal connection, the inventors believe any condition that leads to lowered oxygen delivery (or other such nutrient) to the tissue in and around the eye mediates and/or causes any of a variety of eye diseases, including but not limited to AMD. Possible conditions include but are not limited to one or more of the following: blockage in the internal carotid artery; blockage in the ophthalmic artery; reduced blood flow anywhere in the fluid flow path between the ICA and eye tissue; reduced blood flow rate anywhere in the fluid flow path between the ICA and eye tissue; decreased hemoglobin amount or delivery to one or more eye tissues; and blockage or reduced flow in any of the junctions or ostia between any of the vasculature between the ICA and one or more eye tissues.

The general anatomical area of interest is all of the vasculature that is in the fluid flow path to and from the eye, the rear of the eye, portions of the eye, or regions near the eye. The primary areas of the anatomy include, but are not limited to the Internal Carotid Artery (ICA), the Ophthalmic Artery (OA) and the junction between the ICA and the OA, which is referred to in this disclosure as the ostium. Secondary areas of the anatomy include the vascular system commonly referred to as the terminal branches. These areas include, but are not limited to the Supra Orbital Artery (SOA), the Supra Trochlear Artery (STA), the Dorsal Nasal Artery (DNA), and the Facial Arteries (FA).

Medically and therapeutically, there are also zones of interest: Zone 1 includes the ICA above and below the OA ostium (including the ostium itself); Zone 2 includes the OA from the ostium to the annulus of Zinn; and Zone 3 includes the annulus of Zinn to the terminal OA arteries (e.g., SOA, STA, DNA, and FA).

SUMMARY

The present disclosure addresses some or all of the problems found in current therapies, for example, by improving oxygen delivery to and around the eye. The inventors believe that decreased oxygen, regardless of the cause and even to the point of hypoxia, may be involved or implicated in many eye diseases or conditions.

The present disclosure includes, in certain aspects, methods and devices for restoring or increasing the amount of oxygen that reaches the eye or eye area. Restoring or increasing refers to, for example, removing or opening a blockage (or partial blockage) in one or more vascular systems that support the eye. Opening a blockage or partial blockage refers to, for example, increasing or restoring blood flow to or around the eye. As used herein, increasing blood flow includes but is not limited to increasing the blood flow rate.

The present disclosure, in certain aspects, includes methods for percutaneous access and treatment of vascular structures at the rear of the eye, intended to provide devices and treatment methods for diseases of the eye related to compromised vascular flow. These methods include, but are not limited to, treatment for the symptoms related to Age Related Macular Degeneration (AMD), Glaucoma and Diabetic Retinopathy by placement of a stent in the ICA/OA ostium to provide treatment to stenosis in Ophthalmic/Internal Carotid Artery (ICA/OA) ostium, thereby restoring normal or near normal, or improving blood flow to the rear of the eye, including the retina, choroid and/or associated structures Embodiments of the present disclosure may include delivery of one or more stents positioned in the vasculature supplying blood to the eye, and a stent that is specifically designed for placement in the Internal Carotid Artery (ICA) will reduce the likelihood of thrombotic events due to ICA plaque disruption, places specific support in the ICA/Ophthalmic Artery (OA) ostium to provide patency, and may be designed with radiopaque features to guide in accurate placement.

In accordance with the present disclosure, diseases and conditions of the eye may be directly mediated by compromised blood flow to the vasculature of the posterior eye.

The present disclosure, in certain aspects, is also directed to one or more intravascular medical devices and methods intended to sufficiently unblock or partially restore blood flow in a blocked or partially blocked artery such that oxygen content is increased distal to the blockage. An embodiment of the disclosure is directed to devices and methods for restoring blood flow through the ostium. An embodiment of the disclosure includes using these devices and methods to restore or increase blood flow to the eye or a portion thereof. An embodiment of the present disclosure includes restoring or increasing oxygen levels in the eye or a portion thereof. Restoring or increasing oxygen flow may include using these devices and methods, or equivalent devices and methods, but is not to be limited thereby.

The use of catheter delivery systems for positioning and deploying therapeutic devices, such as balloons, stents and embolic devices, in the vasculature of the human body has become a standard procedure for treating endovascular diseases. It has been found that such devices are particularly useful in treating areas where traditional operational procedures are impossible or pose a great risk to the patient. Advancements in catheter deployment systems have provided an alternative treatment in such cases. Some of the advantages of catheter delivery systems are that they provide methods for treating blood vessels by an approach that has been found to reduce the risk of trauma to the surrounding tissue, and they also allow for treatment of blood vessels that in the past would have been considered inoperable.

A disease target is, for example, Age-Related Macular Degeneration (AMD). In AMD, a lack of blood flow to the posterior eye vasculature may directly reduce healthy levels of $O_2$ as supplied by blood to the choroid. This lack of $O_2$ initiates a cascade of events which begins with thinning of choroidal tissue and ends with symptomatic AMD. While there are some cases of AMD which are genetically related, compromised blood flow acts to initiate and advance the disease in many non-genetic cases and may have a causative role in genetic AMD. It is postulated that the cause of both wet and dry AMD may be linked to reduced blood flow to the back of the eye. There is a literature precedent which establishes a link between coronary artery disease (CAD) and AMD. While this link is well established in modern medical literature, until now, a direct link between supply of oxygen to the posterior ophthalmic vasculature and AMD has not been studied or established.

Human blood vessels often become occluded or blocked to the extent that the blood carrying capacity of the vessel is reduced. Should the blockage occur at a critical place in the circulatory system, serious and permanent injury can occur. To prevent this, some form of medical intervention is usually performed when significant occlusion is detected.

Several procedures are now used to open these stenosed or occluded blood vessels in a patient caused by the deposit of plaque or other material on the walls of the blood vessels. Angioplasty, for example, is a widely known procedure wherein an inflatable balloon is introduced into the occluded region. The balloon is inflated, dilating the occlusion, and thereby increasing the intraluminal diameter.

Another procedure is atherectomy. During atherectomy, a catheter is inserted into a narrowed artery to remove the matter occluding or narrowing the artery, e.g., fatty material. The catheter may include a rotating blade or cutter disposed in the tip thereof. Also located at the tip may be an aperture and a balloon disposed on the opposite side of the catheter tip from the aperture. As the tip is placed in close proximity to the fatty material, the balloon is inflated to force the aperture into contact with the fatty material. When the blade is rotated, portions of the fatty material are shaved off and retained within the interior lumen of the catheter. This process is repeated until a sufficient amount of fatty material is removed and substantially normal blood flow is resumed.

In another procedure, stenosis within arteries and other blood vessels is treated by permanently or temporarily introducing a stent into the stenosed region to open the lumen of the vessel. The stent typically comprises a substantially cylindrical tube or mesh sleeve made from such materials as stainless steel or nitinol. The design of the material permits the diameter of the stent to be radially expanded, while still providing sufficient rigidity such that the stent maintains its shape once it has been enlarged to a desired size.

Embodiments herein relate to methods for percutaneous access and treatment of vascular structures at the rear of the eye, intended to provide devices and treatment methods for diseases of the eye related to compromised vascular flow. These methods include, but are not limited to, treatment for the symptoms related to Age Related Macular Degeneration, Glaucoma and Diabetic Retinopathy (and other vascular related eye diseases) by use of a specially designed vascular filter during stent placement, or with other methods, used to provide interventional treatment to the Ophthalmic/Internal Carotid Artery (OA/ICA) ostium. This filter device is designed to reduce the likelihood of stroke due to dislodgement of vascular material during a procedure. This specially designed filter is an integral part of the treatment methodology for treating any of the vasculature behind the eye.

In one example, a method for treating at least one of an ophthalmic artery or an ostium between the ophthalmic artery and an internal carotid artery of a subject may include delivering a microcatheter to a location within vasculature of the subject. The method may further include delivering a filter to a location within at least one of the ophthalmic artery or the ostium and transitioning the filter between a first delivery configuration and a second deployed configuration. Further, the method may include deploying a stent to a location within the internal carotid artery.

Examples of the method may include any one or more of the following features. The method may further include withdrawing the filter toward the stent. The method may further include aligning an opening of the stent with the ostium. The deploying the stent may include delivering a distal portion of the stent, confirming maintained alignment of the opening of the stent with the ostium, and delivering a proximal portion of the stent after confirming maintained alignment of the opening of the stent with the ostium. The aligning may include observing one or more radiopaque markers of the stent. The transitioning the filter may include one or both of rotating the filter or withdrawing the filter. The method may further include delivering the filter via a central catheter positioned radially within the stent. Prior to the deploying the stent, the stent may be compressed about an external surface of the central catheter. The method may further include withdrawing the central catheter from the stent. The method may further include removing debris from within the at least one of the ophthalmic artery or the ostium.

In another example, a method for treating at least one of an ophthalmic artery or an ostium between the ophthalmic artery and an internal carotid artery of a subject may include extending a filter to a location within the ophthalmic artery and transitioning the filter between a first delivery configuration and a second deployed configuration. The method may further include deploying a stent to a location within the internal carotid artery and removing debris from within the ophthalmic artery.

Examples of the method may include any one or more of the following features. The treating the at least one of the ophthalmic artery or the ostium between the ophthalmic artery and the internal carotid artery may include treating an eye disease, disorder, or condition by restoring or increasing the amount of oxygen available to the eye, or a portion of the eye, or a structure associated with the eye or a portion thereof. The deploying the stent may include aligning an opening of the stent with the ostium. The method may further include restoring or maintaining blood flow through the ophthalmic artery and/or the internal carotid artery. The method may further include increasing an oxygen content of blood flowing to the eye. The deploying the stent may include expanding the stent into contact with a wall of the internal carotid artery. A diameter of the filter in the first delivery configuration may be smaller than a diameter of the filter in the a second deployed configuration.

In a further example, a system for treating at least one of an ophthalmic artery or the ostium between the ophthalmic artery and an internal carotid artery of a subject may include a stent having a proximal portion, a distal portion, and a side-wall opening positioned between the proximal portion and the distal portion. The opening may be configured for alignment with the ostium. The system also may include a central catheter removably positioned within a lumen of the stent. In a first configuration of the stent, the stent may be compressed against a surface of the central catheter, and in a second configuration of the stent, the stent may be expanded away from the surface of the central catheter. Additionally, the system may include a filter wire terminating in a filter moveable relative to the central catheter and capable of transitioning between a first arrangement and a second arrangement.

Examples of the system may include any one or more of the following features. The stent may include one or more radiopaque markers. The stent may have a cross-sectional dimension of between about 2.5 mm to about 5.5 mm and a length ranging between 15 mm to 40 mm.

Both the foregoing general description and the following detailed description are exemplary and explanatory only and are not restrictive of the features, as claimed. As used herein, the terms "comprises," "comprising," "having," "including," or other variations thereof, are intended to cover a non-exclusive inclusion such that a process, method, article, or apparatus that comprises a list of elements does not include only those elements, but may include other elements not expressly listed or inherent to such a process, method, article, or apparatus. Additionally, the term "exemplary" is used herein in the sense of "example," rather than "ideal." As used herein, the terms "about," "substantially," and "approximately," indicate a range of values within +/−5% of the stated value unless otherwise stated.

DETAILED DESCRIPTION

In at least certain embodiments, the present disclosure is directed to restoring and/or increasing the amount of oxygen that is available to one or more parts of the eye or to the eye area. Devices and methods are described.

Restoring and/or increasing the amount of oxygen is used herein to refer to any device, method, therapy, or combination that changes the oxygen content in or near the eye. Examples of such include, but are not limited to, increasing the blood flow anywhere in the vasculature leading to the eye or a portion of the eye; removing or opening an obstruction in the fluid flow path in the vasculature leading to the eye; delivering and deploying a stent in the fluid flow path in the vasculature leading to the eye; using atherectomy or similar devices to physically remove portions of any obstructions in the vasculature leading to the eye or portion of the eye; and localized drug and/or an oxygen device for increasing flow or amount of oxygen in one or more eye tissues. In some embodiments, a device or method of the present disclosure may be combined with a known or new drug or oxygen device in order to treat one or more eye diseases or conditions.

The present disclosure provides for an apparatus for deployment of a detachable diagnostic or therapeutic implant device such as a stent 10, embolic coil, or other vascular occlusion device using a catheter, whereby placement of a stent 10 or the like in a portion of the carotid artery changes the diameter of the internal carotid artery (ICA) 2 and/or the ophthalmic artery (OA) 4, which in turn increases blood flow between the ICA 2 and the eye.

The present disclosure, in at least certain aspects, is directed to restoring and/or increasing the amount of oxygen that is available to one or more parts of the eye or to the eye area, specifically by removing or partially opening a blockage in one or more of the arteries that supplies blood flow to the eye. In embodiments of the disclosure, a blockage is removed or opened in the ICA 2, the OA 4, the ostium 6 (as used herein, referring to the junction between the ICA 2 and the OA 4), or combinations thereof. In embodiments, the devices and methods of the present disclosure involve increasing the blood flow and/or blood flow rate to or near the eye. To or near the eye, as used herein, refers to the vasculature system that supplies blood to the various structures of the eye.

The present disclosure includes methods, devices, and systems for removing a blockage in the ostium, wherein removing the blockage comprises opening a channel or access through the ostium 6 sufficient to provide a therapeutically beneficial amount of oxygen to the eye, the rear of the eye, or portions thereof. The present disclosure also includes restoring and/or improving blood flow anywhere in the vascular pathway to or within the eye.

Another embodiment of the present disclosure includes reducing and/or removing any blockage in the oxygen pathway to the eye. In this and other embodiments of the present disclosure, reducing blockage includes but is not limited to piercing or penetrating the blockage. In embodiments of the present disclosure, piercing and penetrating the blockage refers to obtaining sufficient blood and/or fluid flow through or around the blocked vascular area sufficient to provide a therapeutically beneficial amount of oxygen to the eye or a portion of the eye.

Another embodiment of the present disclosure further includes supplying oxygen to the eye or near the eye, wherein, in this embodiment, the source of the oxygen is external.

Another embodiment of the present disclosure includes one or more medical devices, such as a catheter 30 or the like, and its use to clear or penetrate a blockage in the vascular system that provides oxygen to the eye. In embodiments of the present disclosure, the blockage in the vascular system is a blockage in the junction or ostium 6 between the ICA 2 and the OA 4.

Another embodiment of the present disclosure includes a medical device, such as a stent 10 or the like, that is configured for and may be used to open, clear, or improve vascular flow to or around the eye, wherein vascular flow mediates the amount of oxygen that is delivered to the eye.

Typically, these procedures involve inserting the distal end of a delivery catheter 30 into the vasculature of a patient and guiding it through the vasculature to a predetermined delivery site. A vascular occlusion device may be attached to the end of a delivery member which pushes the occlusion device through the catheter 30 and out of the distal end of the catheter 30 into the delivery site.

For some of these embodiments, one or more layers of the implant device may be configured to anchor or fix the implant device in a clinically beneficial position. For some embodiments, the implant device may be disposed in whole or in part within the vascular defect in order to anchor or fix the device with respect to the vascular structure or defect. The one or more layers of the implant device may be configured to span an opening, neck or other portion of a vascular defect in order to isolate the vascular defect, or a portion thereof, from the patient's nominal vascular system in order to allow the defect to heal or to otherwise minimize the risk of the defect to the patient's health.

The present disclosure also includes a delivery system configured or adapted to position and/or orient the stent 10 in the ostium 6.

An embodiment of the present disclosure includes methods and devices for treating a non-human animal. Some embodiments of the present disclosure include treating a dog, including but not limited to treating central serous retinopathy.

Figure 1A:
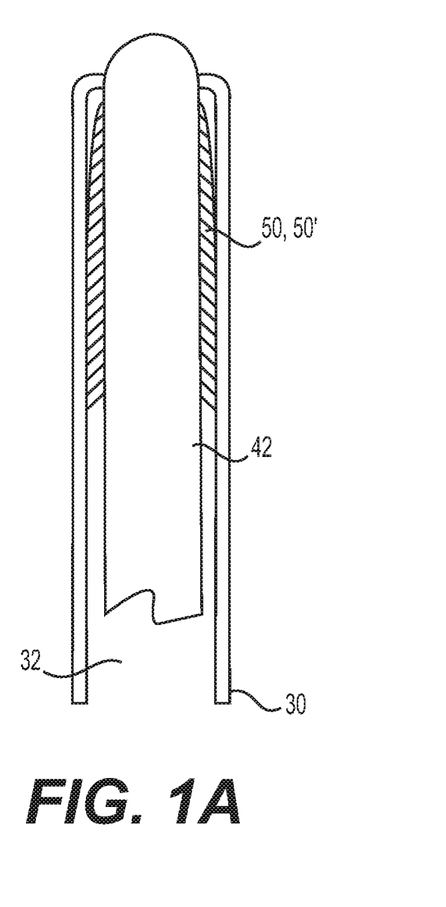
FIG. 1A shows an interventional device of the present disclosure, showing a guidewire with a compressed filter element.

Some embodiments of a delivery system for deployment of an implant device to treat a patient's vasculature include a microcatheter (or delivery catheter) 30 having an inner lumen 32 extending the length thereof. The inner lumen 32 provides a passageway for an implant or other diagnostic or therapeutic device (e.g., stent 10 and/or filter 50) to treat a patient's vasculature. Some implant or therapeutic device embodiments may include one or more self-expanding resilient layers of thin coupled filaments, the layers defining a longitudinal axis between a proximal end and a distal end. Such embodiments can assume a radially-constrained, axially-elongated state configured for delivery through microcatheter 30, with the thin woven filaments extending longitudinally from the proximal end to the distal end being radially adjacent to each other, as shown in FIG. 1A. The delivery system further includes an elongated delivery apparatus having a proximal end and a distal end releasably secured to a proximal portion (e.g., a hub or the like) of the implant or therapeutic device.

Access to a variety of blood vessels of a patient may be established, including arteries such as the femoral artery, the radial artery, and the like, in order to achieve percutaneous access to a vascular defect. In general, the patient may be prepared for surgery, the access artery may be exposed (e.g., via a small surgical incision), and access to the lumen is gained using the Seldinger technique where an introducing needle is used to place a wire over which a dilator, or a series of dilators, may dilate a vessel allowing an access sheath to be inserted into the vessel. This would allow the device to be used percutaneously. With an access sheath in place, a guiding catheter (e.g., catheter 30) is used to provide a safe passageway from the entry site to a region near a treatment site. Exemplary guidewires for vascular use may include the Synchro$^2$® made by Boston Scientific and the Glidewire Gold Neuro® made by MicroVention Terumo. Typical guidewire sizes may include about 0.014 inches (0.36 mm) and about 0.018 inches (0.46 mm). Once the distal end of the microcatheter 30 is positioned at the site, often by locating its distal end through the use of radiopaque marker material and fluoroscopy, the microcatheter 30 is cleared. For example, if a guidewire has been used to position the microcatheter, it may be withdrawn from the microcatheter 30, and then the delivery apparatus may be advanced through the microcatheter 30.

Once the implant or therapeutic device (e.g., stent 10, filter 50, etc.) is deployed at a desired treatment site, the microcatheter 30 may then be withdrawn. Characteristics of the implant or therapeutic device (e.g., stent 10, filter 50, etc.) and delivery apparatus discussed herein generally allow for retraction of the implant or therapeutic device after initial deployment into the vascular defect, but in the case of a permanent implant, before detachment of the implant device. Therefore, it may also be possible and desirable to withdraw or retrieve an initially deployed implant device after the fit within the vascular defect has been evaluated in favor of a differently-sized implant device. The tip of a catheter, such as the microcatheter 30, may be advanced into or adjacent to the vascular site or vascular defect. An example of a suitable microcatheter having an inner lumen diameter of about 0.51 mm to about 0.56 mm is the Rapid Transit® manufactured by Cordis Corporation. Examples of some suitable microcatheters 30 may include microcatheters 30 having an inner lumen 32 diameter of about 0.66 mm to about 0.71 mm, such as the Rebar® by Ev3 Company, the Renegade Hi-Flow® by Boston Scientific Corporation, and the Mass Transit® by Cordis Corporation. Suitable microcatheters 30 having an inner lumen 32 diameter of about 0.79 mm to about 0.84 mm may include the Marksmen® by Chestnut Medical Technologies, Inc. and the Vasco 28® by Balt Extrusion. A suitable microcatheter 30 having an inner lumen 32 diameter of about 1.0 mm to about 1.04 mm includes the Vasco 35® by Balt Extrusion. These microcatheters are listed as exemplary embodiments only, and other suitable microcatheters may also be used with any of the embodiments discussed herein.

It is understood that the present disclosure is not limited solely to changing vascular flow in order to improve or restore the amount of oxygen that is delivered to the eye. For example, in some embodiments of the present disclosure, the vascular flow may be unaffected for the most part, but the amount or concentration of hemoglobin may be increased, thereby increasing the amount of oxygen that may be delivered to the eye. One skilled in the art may recognize, with the teaching of the present disclosure, that there are other biological systems or capabilities that may be used to increase the amount of oxygen that is delivered to the eye.

In accordance with the present disclosure, any process, device, or agent that increases the availability of oxygen to the eye or eye region is included within the scope of the present disclosure. These processes, devices, and agents include, but are not limited to internal sources of oxygen, e.g., through the vascular system. These processes, devices, and agents include, but are not limited to external sources of oxygen, e.g., an injection into the eye or eye region with one or more substances that carry oxygen, a substance that captures or concentrates oxygen, a device that manufactures oxygen, and/or one of more substances that result in an increase in the amount of oxygen.

In some embodiments of the present disclosure, a stent 10, is adapted and configured to be delivered to any predetermined area in the vascular system that supplies oxygen to the eye, e.g., ICA 2. In some embodiments of the present disclosure, the stent 10 (FIGS. 2A-2D) is adapted and configured for placement in the ICA/ophthalmic artery ostium 6.

Stent 10 of the present disclosure may be configured for placement in the vasculature supplying blood to the eye. Exemplary blood vessels include but are not limited to the ICA 2, and the OA 4. Stent 10 may also be configured or adapted for treating an obstruction of the Ophthalmic/Internal Carotid Artery ostium 6, comprising: stent 10 ranging in diameter from about 2.5 mm to about 5.5 mm, with an overall length ranging between 15 mm to 40 mm. The stent 10 may have a tapered diameter to facilitate placement within the vasculature. The stent 10 may be self-expanding, non-expanding, or expandable. In embodiments of the present disclosure in which the stent 10 is expandable, the stent 10 may be expanded using any known expanding element, e.g., a balloon or the like. In some embodiments of the present disclosure, the stent 10 is percutaneously delivered.

The present disclosure is also directed to a system comprising stent 10 and an appropriate delivery apparatus, e.g., microcatheter 30; said system may be used for increasing the amount of oxygenated blood in the eye area.

A system of the present disclosure includes stent 10 configured for placement and function in the ostium 6; microcatheter 30 for delivering the stent 10 to the ostium 6 or near the ostium 6, and any of a number of already known structures and devices typically delivered by microcatheter 30.

A stent 10 of the present disclosure may be constructed from materials commonly used in the design and manufacture of self-expanding stents. These materials include, but are not limited to, Nitinol, chromium cobalt, stainless steel, polymers, and bioresorbable and/or other materials commonly used in the coronary vasculature.

The stent 10 may also include a cover (not shown). The cover could be on the inner diameter, the outer diameter, some combination of location specific (strut or struts). It could be a fabric like covering, liquid, and/or a degrading material.

In some embodiments of the present disclosure, the cover may function to trap particulate in and around the area of the stent 10. In this embodiment of the present disclosure, the cover is believed to reduce the potential for inducing thrombosis. In other embodiments of the present disclosure, the stent 10 may include one or more anti-stenosis agents. In other embodiments, the stent may include both functions.

The cover may be formed from PTFE, ePTFE, or other commonly used materials designed to be affixed to the outer and/or inner diameter of the stent 10 with the purpose of providing a method of retaining plaque (or stenotic material) as the stent is expanded against the artery. This cover material is designed to expand with the stent 10 and trap material potentially loosened by the dilatation effect of the stent 10 between the cover and the vascular wall.

The stent 10 or the cover may also include one of more markers, typically radiopaque markers. The stent or cover may be coated or impregnated with one or more radiopaque markers 13 to aid in the proper placement of the stent within the target anatomy, e.g., the ostium 6 of the ICA 2 and the OA 4. Target anatomy, as used herein, refers to any place in the vascular system supplying blood to the eye, including but not limited to the ostium of the ICA 2 and OA 4.

In some embodiments, the stent 10 or its associated covering is designed to provide an opening 11 for accommodation of the ostium 6 such that the material does not block access to the ostium 6 (e.g., the opening 11 is dimensionally compatible with the opening of ostium 6). In some embodiments of the present disclosure, the opening 11 is an area of the stent 10 that is free of stent struts and is unobscured by the stent cover. An exemplary opening 11 is shown in the FIGS. 2B-2D. As shown, the opening of the stent 10 (and any associated stent cover) is configured to correspond or align with complementary markers integrated into the microcatheter 30. These markers are designed to facilitate proper placement of the stent 10 within the anatomy such that the ostium 6 is not blocked by the stent/stent cover material.

In another embodiment, the stent 10 is disposed within a delivery microcatheter 30 and delivery sheath, said microcatheter 30 having a means of providing a single radiopaque marker or plurality of radiopaque markers to aid in the positioning the stent 10 in the appropriate anatomical location within the target anatomy.

In another embodiment, the stent 10 is designed to deploy (e.g., via self-expansion) such that the distal portion of the stent 10 deploys first and aids in anchoring the stent 10 prior to deployment of the proximal section of the stent 10. This may enable the physician to accurately place the stent 10 within the target anatomy. The stent 10 is first placed in the desired location, and then fully delivered.

In another embodiment, the stent 10 is designed with an asymmetrical feature that exerts additional diametric force in the area of the ostium 6.

The stent 10 of the present disclosure may be delivered using any medically appropriate route and/or technique. Suitable routes include but are not limited to subclavian, brachial, and/or direct common carotid access. In an embodiment, the device and system is configured for percutaneous access of the ICA 2 via a femoral approach, as well as other typical percutaneous access locations.

In another embodiment, the system is configured to be used with commonly available coronary guide wire products in styles and size ranges.

A stent 10 or stent cover of the present disclosure may be configured to be visible using non-invasive imaging techniques (e.g., fluoroscopy, etc.). In this embodiment of the present disclosure, the stent 10 and/or cover may include one of more elements to assist in positioning and deploying the stent 10.

In use, the stent 10 is mounted on a central catheter 34 within microcatheter 30 by means of an outer sheath 33 that compresses and holds the stent 10 against a portion of the central catheter 34 to aid in the delivery of the stent 10 to the desired anatomy. Controlled removal of the sheath 33 may provide for the ability to deliver the stent 10 to the desired anatomical location. The sheath 33 may include a mechanical element to allow for controlled advancement and/or retraction of the stent 10. The sheath also may have radiopaque markings to aid in the positioning and delivery of the stent 10.

Figure 2A:
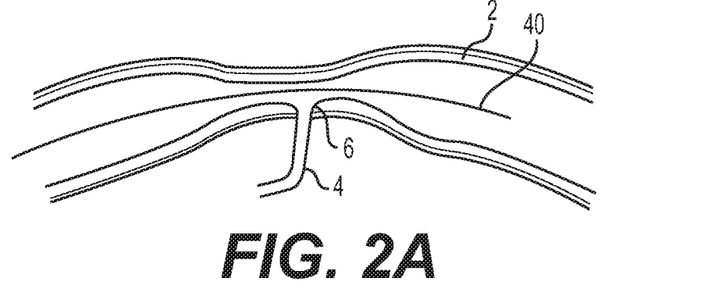
FIG. 2A shows the guidewire placement in the ICA in relation to the OA.
Figure 2B:
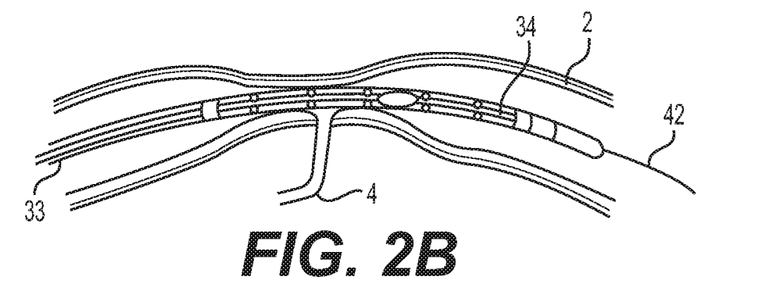
FIG. 2B shows the filter wire in the ICA and placement of a stent near the junction with the OA.
Figure 2C:
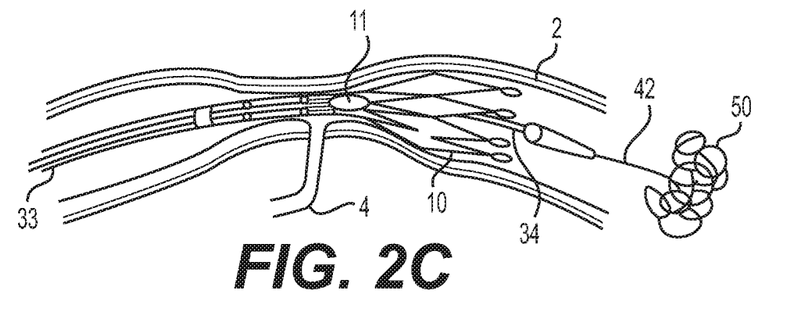
FIG. 2C shows deployment of the stent and deployment of a filter element in the ICA.
Figure 2D:
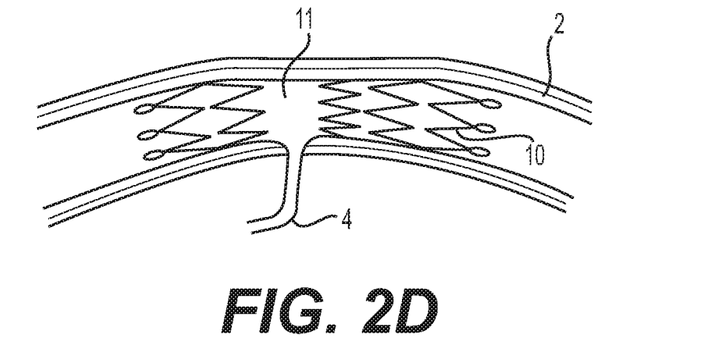
FIG. 2D shows the stent expanded in the ICA after removal of the filter element from the ICA.

As shown in FIG. 2A, a guidewire 40 may be delivered via any appropriate means to a target location within the vasculature. Once so positioned, sheath 33, central catheter 34, stent 10, and microcatheter 30 (not shown in FIGS. 2A-2D) may be advanced over guidewire 40 (e.g., via a lumen of central catheter 34), as shown in FIG. 2B. Alternatively, microcatheter 30 first may be delivered to the site over the guidewire 40, followed by sheath 33 and central catheter 34 carrying stent 10. Once proper placement is achieved, the guidewire 40 may be removed and replaced with a filter wire 42, as shown in FIG. 2B. The filter wire 42 may be deployed such that an optional filtering capability (e.g., via filter 50) is placed distal to the ostium 6 and outside of the field of stent 10 deployment. Once in the proper position, the filter 50 may be deployed such that filtering capability is provided, as shown in FIG. 2C. The stent 10 is then manipulated with the aid of the radiopaque markings such that the ostium 6 will not be obscured by the stent 10 (e.g., such that opening 11 is aligned with ostium 6). The stent 10 is then deployed by slowly retracting the sheath 33 overlying stent 1030, as shown in FIG. 2C. Retracting the sheath 33 may be aided by radiopaque markings on the sheath as well as markings on the stent 10. The distal portion of the stent 10 is delivered first to ensure the ostium 6 will not be blocked. Once distal portion of the stent 10 is in place and/or delivered to a desired location, observation of a non-blocked ostium 6 is confirmed and the proximal portion of the stent 10 is delivered. Next, the filter wire 42, filter 50, and any captured debris is withdrawn into the microcatheter 30 and removed. FIG. 2D shows the stent 10 positioned in the ICA 2 with the opening 11 aligned with the ostium 6 between the ICA 2 and the OA 4.

The present disclosure is also directed to a system comprising one or more medical devices, (e.g., a stent 10) and its delivery apparatus; said system is used for increasing the amount of oxygenated blood in the eye area, or for increasing the amount of oxygen that is or can be delivered to the eye. The present disclosure may also include this system, device, or method in combination with one or more agents or devices for improving vascular blood flow between the common carotid artery and a central artery of the retina; and/or one or more agents for improving vascular blood flow at the ostium 6 and within the OA 4.

The present disclosure further includes the use of one of more diagnostic devices or agents that allow a person to monitor oxygen content in the eye.

In another embodiment, a medical device or agent is capable of delivering drugs to the ostium 6 for the purpose of improving vascular blood flow at the ostium 6 and within the OA 4. These drugs may include (but are not limited to) low dose Viagra (or equivalent RPE inhibitor), Lucentis, Avastin, Taxol, Rapamyacin or other pharmaceuticals used to improve vascular blood flow.

Figure 3A:
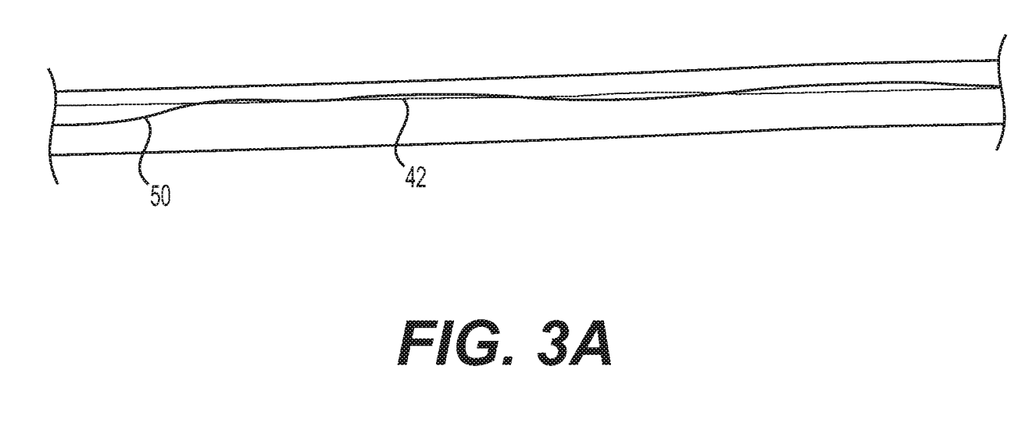
FIG. 3A shows the filter wire in a delivery position.
Figure 3B:
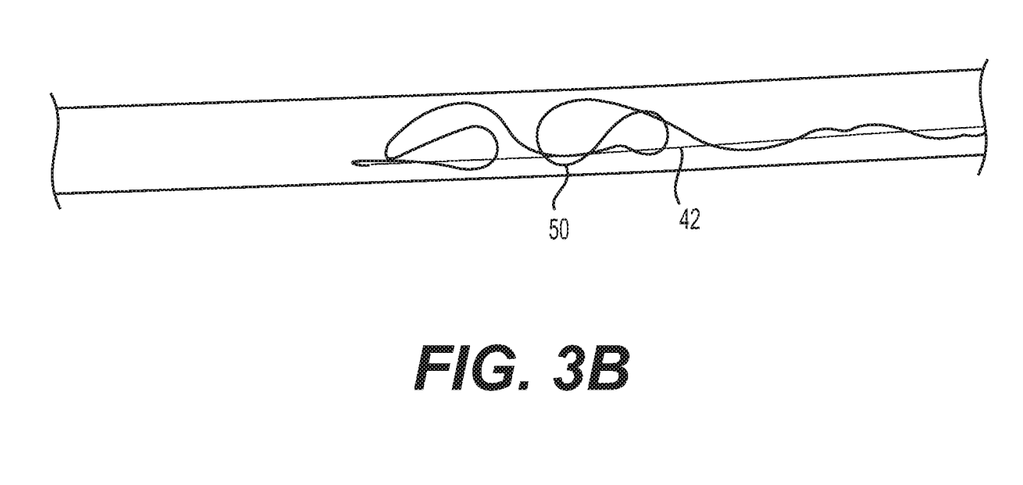
FIG. 3B shows the filter wire in a deployed position.

In an embodiment of the filter 50, the device provides distal emboli protection as part of the stent delivery system (but not limited to stents). Indeed, the filter wire 42 (which also may serve as a guidewire 42), as shown in FIG. 2B, is designed with an overall length intended to facilitate the appropriate anatomical approach, e.g., femoral access would be about 180 cm in overall length. Other access points would use a guidewire/filter wire 42 with an overall length appropriate for their respective access locations. The diameter of a distalmost segment of the wire 42 may range from about 0.008" to about 0.014". Filter wire 42 may include Nitinol material, or the like. The filter wire 42 may have a filter 50 element attached (or monolithically and integrally formed therewith) at a distal end thereof, which may be composed of expanded polyester thread, suture material, or equivalent. The filter 50 may continue alongside the filter wire 42 (e.g., in a generally parallel fashion) (as shown in FIG. 3A) except for a proximalmost portion of a delivery system (e.g., microcatheter 30) nearest the user. A tip (e.g., a distalmost end of filter wire 42 coupled to filter 50) of the guidewire/filter wire 42 is positioned distal to the delivery system (e.g., microcatheter 30) such that it will not interfere with the stent 10 delivery, but will be in close enough approximation so as to effectively provide debris capture capability. Once in the desired location, the guidewire 42 is slightly withdrawn while simultaneously rotated so as to place the filter 50 in a random coiled circular pattern (e.g., a bunched, longitudinally shortened configuration) within the vasculature, as shown in FIGS. 2C and 3B. This arrangement serves to provide filtering capability for any potentially dislodged material during stent deployment. The filter 50 may be treated with a platelet aggregation compound, such as nitric oxide, to reduce the likelihood of platelet aggregation (clotting or thrombus formation) and may be imparted with a specific electrical charge to facilitate attraction of debris to the filter 50 and/or filter wire 42. Removal of the filter 50 (and any trapped material) is accomplished by slight advancement of the delivery catheter (e.g., microcatheter 30) and/or withdrawing the filter 50 into the delivery catheter (e.g., microcatheter 30). It is understood that the direction of filter 50 in FIGS. 3A and 3B is reversed relative to the direction of filter 50 in FIGS. 2B and 2C. That is, a distal end of filter 50 is positioned to the left in FIGS. 3A and 3B while a distal end of filter 50 is positioned to the right in FIGS. 2B and 2C.

In another embodiment, the filter wire 42 is used in conjunction with several other components, including a delivery sheath 33 with mounted stent 10 on a central catheter 34. The central catheter 34 may incorporate a through lumen intended to facilitate the use of a common guidewire to aid in positioning the device within the target vasculature. Once proper placement is achieved, the common guidewire is removed and replaced with a filter wire 42, as described above in connection with FIGS. 2A-2C. The filter wire 42 is deployed such that the filtering capability is placed distal to the ostium 6 and outside of the field of stent 10 deployment. Once in the proper position, the filter 50 is deployed such that filtering capability is provided. The stent 10 is then manipulated and deployed. Once the stent 10 is in place, the filter wire 42 and any captured debris is withdrawn into the sheath 33 or microcatheter 30 and the system removed.

Figure 1B:
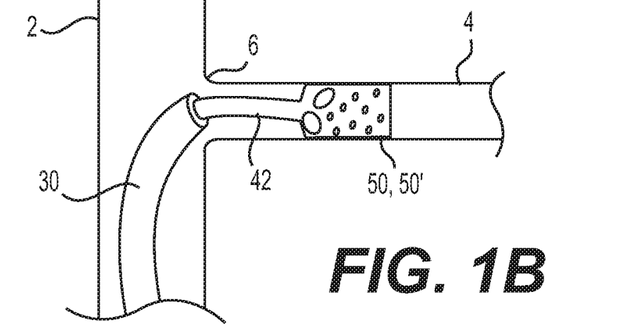
FIG. 1B shows the guidewire and filter of FIG. 1A deployed in the ophthalmic artery.
Figure 1C:
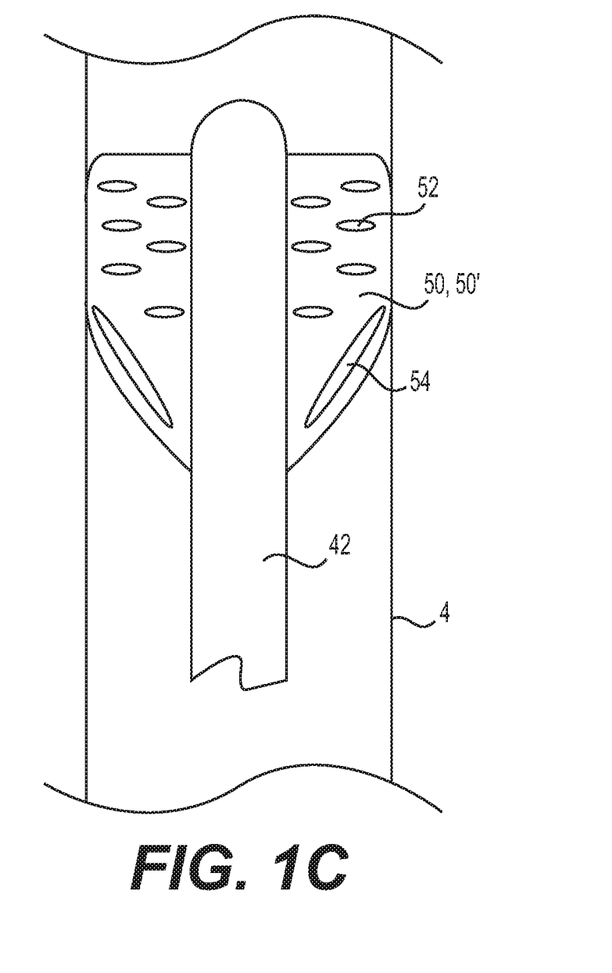
FIG. 1C shows a close-up view of an exemplary ophthalmic artery filter of the present disclosure.

An embodiment of a device and system of the present disclosure includes a filter element 50' configured and adapted for deployment in the OA 4. An exemplary configuration is shown in FIGS. 1A-1C. FIG. 1A shows the filter 50' compressed around a guidewire/filter wire 42, and positioned within a lumen 32 of microcatheter 30. FIG. 1B shows an example of a suitable deployment of the filter 50' in the OA 4. Microcatheter 30 may be positioned in the ICA 2 (as shown) or may be extended into the ostium 6 and/or further into the OA 4. The filter 50' may be deployed in the OA 4 (as shown) or may be deployed at any position between the ostium 6 and further into the OA 4.

FIG. 1C shows a close-up of an exemplary filter 50' configured for use and deployment in the OA. As illustrated, the filter 50' may include one or more micropores 52, 54, typically for capturing, collecting, and removing debris. In the illustrated embodiment, some of the micropores 52 capture debris or allow debris to enter the filter; other micropores 54 allow blood to pass by and through the filter 50'.

In one embodiment, the ophthalmological disease or disorder treated or prevented by any of the methods or compositions described herein is age-related macular degeneration. Vision changes that can be associated with macular degeneration include distortions and/or blind spots (scotoma) detected using an Amsler grid, changes in dark adaptation (diagnostic of rod cell health), changes in color interpretation (diagnostic of cone cell health), or a decrease in visual acuity. Examples of age-related macular degeneration are normeovascular (also known as "dry") and neovascular (also known as "wet" or "exudative") macular degeneration.

In one embodiment, the dry age-related macular degeneration is associated with the formation of drusen. In one embodiment, treating or preventing dry macular degeneration encompasses treating or preventing an abnormality of the retinal pigment epithelium and/or underlying vasculature, known as choriocapilaries. Examples of abnormalities of the retinal pigment epithelium include geographic atrophy, non-geographic atrophy, focal hypopigmentation, and focal hyperpigmentation. In another embodiment, treating or preventing wet age-related macular degeneration encompasses treating or preventing choroidal neovascularization or pigment epithelial detachment.

In some embodiments, wet age-related macular degeneration is classified according to the appearance of its choroidal neovascularization (CNV), into classic, occult or mixed (classic and occult) CNV types, as determined by an angiography, known as fluorescence angiography. Classic, occult or mixed (classic and occult) CNV classification can be based on the time, intensity and level of definition of dye appearance, and leakage from the CNV, as assessed by the fluorescein angiography. In some embodiments, the subject has classic CNV (e.g., pure classic) or mixed CNV (predominantly or minimally classic CNV). In some embodiments, the subject has occult CNV (e.g., pure occult CNV).

In certain embodiments, the ophthalmological disease or disorder is a cataract (e.g., age-related cataract), diabetic macula edema, macular telangiectasia (e.g., type 1 or 2 macular telangiectasia), atrophic macular degeneration, chorioretinopathy (e.g., central serous chorioretinopathy), retinal inflammatory vasculopathy, pathological retinal angiogenesis, age-related maculopathy, retinoblastoma, Pseudoxanthoma elasticum, a vitreoretinal disease, choroidal sub-retinal neovascularization, central serous chorioretinopathy, ischemic retinopathy, hypertensive retinopathy or diabetic retinopathy (e.g., nonproliferative or proliferative diabetic retinopathy, such as macular edema or macular ischemia), retinopathy of prematurity (e.g., associated with abnormal growth of blood vessels in the vascular bed supporting the developing retina), venous occlusive disease (e.g., a retinal vein occlusion, branch retinal vein occlusion or central retinal vein occlusion), arterial occlusive disease (e.g., branch retinal artery occlusion (BRAO), central retinal artery occlusion or ocular ischemic syndrome), central serous chorioretinopathy (CSC), cystoid macular edema (CME) (e.g., affecting the central retina or macula, or after cataract surgery), retinal telangiectasia (e.g., characterized by dilation and tortuosity of retinal vessels and formation of multiple aneurysms, idiopathic JXT, Leber's miliary aneurysms, or Coats' disease), arterial macroaneurysm, retinal angiomatosis, radiation-induced retinopathy (RIRP), or rubeosis iridis (e.g., associated with the formation of neovascular glaucoma, diabetic retinopathy, central retinal vein occlusion, ocular ischemic syndrome, or chronic retinal detachment).

Embodiments of the present disclosure and the various components or elements thereof can be used interchangeably so that features and functions of one exemplary embodiment of a filter device can be used with other embodiments of the filter device. Illustratively, the restraining members or mechanisms of the described embodiments of the present disclosure can be used with multiple different configurations of the filter 50, 50' device. Further, exemplary capture catheters 30 can be used interchangeably such that any capture catheter can be used with any of the described filter 50, 50' devices and such other that may be known to those skilled in the art in light of the teaching contained herein. Additionally, methods of using one embodiment of the present disclosure can be used with other embodiments of the present disclosure. Therefore, embodiments of the present disclosure provide filter 50, 50' devices that have small or low profiles, few parts and components, are simple to manufacture and use, are able to be easily inserted into a patient, be steerable through the tortuous anatomy of a patient, provide filtering capabilities, provide exchange capability so other medical devices can be advanced over or along the filter device, and be capable of removing captured material without allowing such material to escape during filter retrieval.

EXAMPLES

Example 1

Compromised blood flow to the vasculature of the posterior eye may directly contribute to diseases of the eye. This lack of normal blood flow may originate in the ICA 2, the OA 4, branches of the OA 4, and/or combinations thereof, and be directly caused by a blockage in one or more of these vessels. This lack of sufficient blood flow may directly contribute to inadequate oxygen levels seen in tissues such as the choroid, retina, optic nerve and other ophthalmic anatomy. This blockage may manifest as stenosis, lesions or other physiology within the ophthalmic related vasculature and compromise normal blood flow such that the posterior eye vasculature does not receive an adequate oxygen supply for maintenance of normal function. As a result of this reduction of oxygen, it is possible for a cascade of events to begin which may result in various diseases of the eye.

Blood flow was measured for healthy controls and diseased patients (with confirmed AMD diagnosis). Flow rates were measured for the Left Ophthalmic Artery (LOA), Right Ophthalmic Artery (ROA), Left Internal Carotid Artery (LICA) and Right Internal Carotid Artery (RICA) using a Phased Contrast Magnetic Resonance Imaging (PCMRI) technique. These flow rates were measured in cm/sec. The average size of the ICA was 4.66 mm and the average size of the OA was 1.00 mm.

Specific flow rates were compared, and the OA flow data showed a medically or clinically observable difference between the flow rates for healthy controls compared to diseased patients. Specific flow rates were compared, and the ICA flow data showed a medically or clinically observable difference between the flow rates for healthy controls compared to diseased patients. In every case, the blood flow rate for the diseased patients appears to be lower than the blood flow rate for the healthy controls.

Example 2

Cadaveric tissue samples were obtained with confirmed diagnosis of CAD with no diagnosis of AMD. Visual confirmation of the presence of stenosis in the ophthalmic/internal carotid ostium of the samples was performed. One sample had extensive stenosis that appeared to completely block the OA in both the left and right ICA/OC ostiums. It should be noted that the left OA, as observed branching off the ICA, was much smaller in diameter than that of a typical OA, almost to the point of being non-existent. This sample was diagnosed with CAD, CHF, PAD, HTN and 4× bypass Sx.

A different sample had what appeared to be early stage stenosis accumulation in both the left and right ICA/OA ostiums as confirmed by visual observation. None of these stenosis appeared to cause blockage in the OA of either ostium. This sample was diagnosed with CAD, chronic anemia, Buerger's disease, thromboembolic disease and extensive DVT.

Example 3

In another sample the right ICA was removed and the ostium was visually examined. A blockage of the OA at the ostium was confirmed and appeared to be complete. Once the section of left ICA was removed, internal access to the OA ostium was gained, and a micro PTCA balloon catheter was inserted. This test was performed to visually observe the effect of placing and inflating a balloon catheter in the OA. This (non-compliant) balloon catheter has a maximum diameter of 0.85 mm at 16 atms, with a crossing profile of 0.74 mm and a working length of approximately 5 mm. The balloon was inflated several times to approximately 12 atms max, and the balloon was observed through the vessel. The vessel appeared to tolerate the inflations without obvious damage.

We claim:

1. A method for treating at least one of an ophthalmic artery or an ostium between the ophthalmic artery and an internal carotid artery of a subject, comprising:
    delivering a microcatheter to a location within vasculature of the subject;
    delivering a filter to a location within at least one of the ophthalmic artery or the ostium;
    transitioning the filter between a first delivery configuration and a second deployed configuration; and
    deploying a stent to a location within the internal carotid artery.

2. The method of claim 1, further including withdrawing the filter toward the stent.

3. The method of claim 1, further including aligning an opening of the stent with the ostium.

4. The method of claim 3, wherein the deploying the stent includes delivering a distal portion of the stent, confirming maintained alignment of the opening of the stent with the ostium, and delivering a proximal portion of the stent after confirming maintained alignment of the opening of the stent with the ostium.

5. The method of claim 3, wherein the aligning includes observing one or more radiopaque markers of the stent.

6. The method of claim 1, wherein the transitioning the filter includes one or both of rotating the filter or withdrawing the filter.

7. The method of claim 1, further including delivering the filter via a central catheter positioned radially within the stent.

8. The method of claim 7, wherein, prior to the deploying the stent, the stent is compressed about an external surface of the central catheter.

9. The method of claim 7, further including withdrawing the central catheter from the stent.

10. The method of claim 1, further including removing debris from within the at least one of the ophthalmic artery or the ostium.

11. A method for treating at least one of an ophthalmic artery or an ostium between the ophthalmic artery and an internal carotid artery of a subject, comprising:
    extending a filter to a location within the ophthalmic artery;
    transitioning the filter between a first delivery configuration and a second deployed configuration;
    deploying a stent to a location within the internal carotid artery;
    removing debris from within the ophthalmic artery.

12. The method of claim 11, wherein treating the at least one of the ophthalmic artery or the ostium between the ophthalmic artery and the internal carotid artery includes treating an eye disease, disorder, or condition by restoring or increasing the amount of oxygen available to the eye, or a portion of the eye, or a structure associated with the eye or a portion thereof.

13. The method of claim 11, wherein the deploying the stent includes aligning an opening of the stent with the ostium.

14. The method of claim 11, further including restoring or maintaining blood flow through the ophthalmic artery and/or the internal carotid artery.

15. The method of claim 11, further including increasing an oxygen content of blood flowing to the eye.

16. The method of claim 11, wherein the deploying the stent includes expanding the stent into contact with a wall of the internal carotid artery.

17. The method of claim 11, wherein a diameter of the filter in the first delivery configuration is smaller than a diameter of the filter in the a second deployed configuration.

* * * * *

UNITED STATES PATENT AND TRADEMARK OFFICE
CERTIFICATE OF CORRECTION

| | | |
|---|---|---|
| PATENT NO. | : 11,278,389 B2 | |
| APPLICATION NO. | : 16/467318 | |
| DATED | : March 22, 2022 | |
| INVENTOR(S) | : Calhoun et al. | |

It is certified that error appears in the above-identified patent and that said Letters Patent is hereby corrected as shown below:

In the Claims

In Claim 17, Column 16, Line 46, "the a" should read as --the--.

Signed and Sealed this
Thirty-first Day of May, 2022

Katherine Kelly Vidal
*Director of the United States Patent and Trademark Office*